US 8,540,969 B2

United States Patent
Loxley et al.

(10) Patent No.: US 8,540,969 B2
(45) Date of Patent: Sep. 24, 2013

(54) AEROSOL DISPERSIONS OF PARTICLES WITH ACTIVE PHARMACEUTICAL INGREDIENTS

(75) Inventors: Andrew Loxley, Philadelphia, PA (US); Ismar Dizdarevic, Nutley, NJ (US); Mark Mitchnick, East Hampton, NY (US)

(73) Assignee: Particle Sciences, Inc., Bethlehem, PA (US)

( * ) Notice: Subject to any disclaimer, the term of this patent is extended or adjusted under 35 U.S.C. 154(b) by 599 days.

(21) Appl. No.: 12/596,508

(22) PCT Filed: Apr. 18, 2008

(86) PCT No.: PCT/US2008/060742
§ 371 (c)(1),
(2), (4) Date: Nov. 19, 2009

(87) PCT Pub. No.: WO2008/131170
PCT Pub. Date: Oct. 30, 2008

(65) Prior Publication Data
US 2010/0124535 A1     May 20, 2010

Related U.S. Application Data

(60) Provisional application No. 60/912,523, filed on Apr. 18, 2007.

(51) Int. Cl.
*A61K 9/12* (2006.01)
*A61K 9/127* (2006.01)
*A61K 9/133* (2006.01)
*A61K 9/14* (2006.01)

(52) U.S. Cl.
USPC .................... 424/45; 424/489; 424/450

(58) Field of Classification Search
USPC ............................. 424/45, 489, 450
See application file for complete search history.

(56) References Cited

U.S. PATENT DOCUMENTS

| 4,329,787 A | 5/1982 | Newton ............... 34/1 |
| 6,264,922 B1 | 7/2001 | Wood et al. ............ 424/45 |
| 6,811,767 B1 * | 11/2004 | Bosch et al. ........... 424/45 |
| 2005/0244339 A1 | 11/2005 | Jauernig et al. ......... 424/45 |

FOREIGN PATENT DOCUMENTS

| WO | WO 94/20027 | 9/1994 |

OTHER PUBLICATIONS

Kawashima et al. "Pulmonary Delivery of Insulin with Nebulized DL-Lactide/Glycolide Copolymer (PLGA) Nanospheres to Prolong Hypoglycemic Effect" Journal of Controlled Release 1999 vol. 62: 279-287.
Rudolph et al. "Application of Novel Solid Lipid Nanoparticle (SLN)—Gene Vector Formulations Based on a Dimeric HIV-1 TAT-Peptide in Vitro and in Vivo" Pharmaceutical Research 2004 vol. 21 (9): 1662-1669.

* cited by examiner

*Primary Examiner* — Mina Haghighatian
(74) *Attorney, Agent, or Firm* — Licata & Tyrrell P.C.

(57) ABSTRACT

Aerosols containing a plurality of aqueous droplets, each droplet containing on average at least one essentially-neutral particle sized to fit within the droplet are provided. Aerosols wherein an active pharmaceutical ingredient is attached to, or otherwise incorporated in the essentially neutral particles are also provided. Methods for administering an active pharmaceutical ingredient to a subject in need thereof via inhalation of these aerosols, preferably via nebulizer, are also provided.

15 Claims, 2 Drawing Sheets

AEROSOL DISPERSIONS OF PARTICLES WITH ACTIVE PHARMACEUTICAL INGREDIENTS

This patent application is the U.S. National Stage of International Application No. PCT/US2008/060742, filed Apr. 18, 2008, which claims the benefit of priority from U.S. Provisional Application Ser. No. 60/912,523 filed Apr. 18, 2007, teachings of each of which are herein incorporated by reference in their entirety.

FIELD OF THE INVENTION

The present invention relates to aerosols composed of essentially neutral colloidal particles sized to fit within the aqueous droplets of the aerosols. Preferred is that one or more active pharmaceutical ingredients be encapsulated by and/or attached to the colloidal particles. The present invention also relates to methods for use of these aerosols to deliver one or more active pharmaceutical ingredients to a subject via inhalation.

BACKGROUND OF THE INVENTION

The inhalation route, employed primarily in the past for drugs acting in the respiratory tract, is now being extended for systemic drug delivery.

Water soluble drugs can be delivered to the lungs in droplets produced by aerosolizing a solution of the drug, using a nebulizer to generate and aerosolize the droplets. The aerosol formed by the nebulizer has a droplet size of approximately 1 to 50 microns, more commonly 1 to 10 microns in diameter, ideal for delivery to the lungs. For example, ribavirin (virazole) is a relatively water soluble drug (142 mg/mL) delivered via nebulizer in hospitals for treatment of respiratory syncytial virus and other viral diseases. However, this drug crystallizes wherever the nebulized mist lands, including but not limited to equipment, bedding, and the patient, thus creating a hazard to health workers, especially pregnant women.

Delivery of poorly water-soluble drugs presents an even bigger problem for aqueous aerosol delivery to the lungs as large drug particles block the nebulizer orifice.

Thus, there is a need for inhalation formulations with improved deposition efficiency, targeting, trafficking through the mucus membrane, bioavailability, stability, particularly for higher solid formulations, and sustained release for inhaled drugs.

Various particle engineering methods have been developed to improve inhalation formulations.

For example, spray freeze drying into liquids, supercritical fluid technology, and crystal engineering, are being developed to overcome limitations of conventional methods of spray drying and jet milling.

Various engineered particles such as amorphous glass particles for protein stabilization, spray-dried oligosaccharides and large porous particles for sustained delivery, and nanocrystals for improved cellular penetration, are also being developed.

In addition, new dry powder and liquid aerosol inhalation devices, such as the Nektar DPI system, AERx® (Aradigm), Spiros® (Dura Pharmaceuticals), and the Respimat® (Boehringer Ingelheim) which improve deposition efficiency, ease of use, and/or reproducibility of dose have been developed.

SiRNA and poly(ethylene imine) (PEI), a water soluble polymer, form a complex in aqueous solution which has been nebulized and delivered into mice lungs, with activity of the SiRNA being maintained. Maintaining activity of siRNA can be problematic since SiRNA requires protection from nucleases as well as an appropriate delivery vector which allows for entry of siRNA into the cell followed by endosomal escape so that it can function in the cytosol of the cell.

U.S. Pat. No. 6,264,922 describes nebulized aerosols containing a nanoparticle dispersion of insoluble therapeutic or diagnostic agent particles having a surface modifier on the surface thereof.

Rudolph et el. (*Pharmaceutical Research* 2004 21(9): 1662-1669) describe an aqueous dispersion of solid lipid nanoparticles (SLN) of cetylpalmitate and the cationic lipid N,N-di-($\beta$-stearoylethyl)-N,N-dimethyl-ammonium chloride or 1,2-dioleyl-sn-glycero-3-trimethylammoniumpropane (DOTAP) to which DNA was adsorbed to the surface for lung delivery. They showed expression of the DNA-encoded protein after delivery from a nebulized aerosol to the lungs of mice.

Kawashima et al. discloses dispersions of PLGA nanoparticles containing insulin prepared by a modified emulsion solvent diffusion method in water, and delivered by nebulizer to the lungs of guinea pigs (Kawashima et al. Journal of Controlled Release 1999 62, no. 1-2 (6 ref.):279-287).

WO 94/20072 discloses colloidal solid lipid particles primarily for parenteral administration of preferably poorly water soluble bioactive substances.

SUMMARY OF THE INVENTION

An aspect of the present invention relates to an aerosol comprising a plurality of aqueous droplets, each droplet comprising an essentially neutral colloidal particle sized to fit inside the droplet, said particle being stabilized by an amphiphile.

Another aspect of the present invention relates to an aerosol for delivery of one or more active pharmaceutical agents comprising a plurality of aqueous droplets, each droplet comprising an essentially neutral colloidal particle sized to fit inside the droplet and an active pharmaceutical agent incorporated within or attached to the particle.

Another aspect of the present invention relates to methods for producing formulations for administration of an active pharmaceutical agent via an inhaled aerosol comprising a plurality of aqueous droplets, each droplet comprising an essentially neutral colloidal particle sized to fit inside the droplet, said particle being stabilized by an amphiphile.

Another aspect of the present invention relates to a method for treating a subject in need of an active pharmaceutical agent comprising administering to the subject via inhalation an aerosol comprising a plurality of aqueous droplets, each droplet comprising an essentially neutral colloidal particle sized to fit inside the droplet and active pharmaceutical agents incorporated within or attached to the particle.

DETAILED DESCRIPTION OF THE INVENTION

Figure 1:
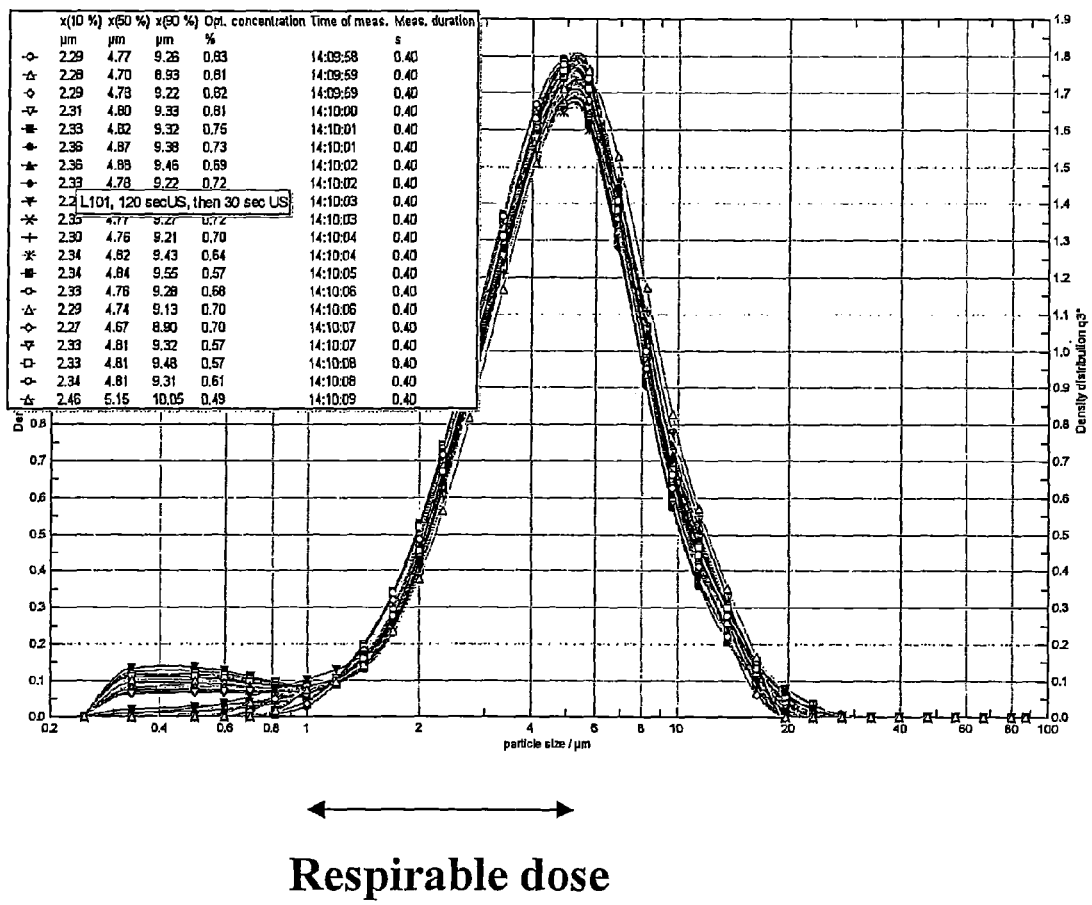
FIG. 1 is a line graph showing the droplet size of the aerosol of the present invention produced by an over the counter (OTC) nebulizer to be ideal for pulmonary delivery.

The present invention provides therapeutically useful inhalable particulate dispersions as well as methods for their production and use.

Thus, one aspect of the present invention relates to aerosols. An aerosol of the present invention comprises a plurality of aqueous droplets, wherein each aqueous droplet of the plurality comprises an essentially neutral colloidal particle sized to fit inside the droplet. The aerosol is generated from an aqueous dispersion of the essentially neutral colloidal particles in an aqueous solution. On average each droplet contains at least one essentially neutral particle sized to fit within the droplet. The aerosol may further comprise aqueous droplets which contain no particles.

Examples of aqueous solutions for use in the present invention include but are not limited to water and phosphate buffered saline. Also useful in the present invention are HFA (hydrofluoro alkanes), silicones, or other liquids immiscible with the particles and/or drug, non-degrading to the nebulizer, and non-toxic to the patient.

Means for generating the aerosol include, but are not limited to nebulizers, metered dose inhalers, atomizers that having vibrating plates drilled with many holes and ultrasonic atomizers.

In a preferred embodiment, the aqueous droplet of the aerosol is sized for optimal pulmonary delivery to a subject. Thus, preferred are aerosols with aqueous droplets of 50 microns or less, more preferably less than 10 microns. In some embodiment, the droplets may be less than 100 nm.

Accordingly, to fit inside the droplets, the essentially neutral particles are sized smaller than the aqueous droplets. In general, particles of about 1 micron or less are used. A preferred range for the particles is from about 10 nm to about 1000 nm.

Example of particles for the essentially neutral colloidal particles used in the present invention include, but are not limited to, particles comprising polymers such as, but not limited to PLGA, PLLA, and poly(caprolactone), solid lipid particles such as, but not limited to, cholesterol, esters of higher fatty acids, fatty alcohols and fatty amines, a pharmaceutically acceptable oil (dispersion is an oil-in-water emulsion), natural or synthetic waxes such as, but not limited to, carnauba wax, beeswax and emulsifying wax, micelles made from amphiphiles such as, but not limited to alkyl-polyethers, polyoxyethylene sorbitan fatty acid esters (Tweens), polyoxyethylene alkyl ethers (Brijs), and PEO-PPO-PEO (Pluronics), vesicles such as liposomes made from phospholipids such as lecithin, polymerosomes made from self assembly of diblock copolymers containing a hydrophilic block such as PEO and a hydrophobic block such as a polyester, cells, viruses, polyplexes, coacervates such as, but not limited to, those formed between dilute solutions of gelatin and gum acacia made in the presence of the dissolved or dispersed pharmaceutically active agent, or inorganic particles and carbon nanotubes.

By "essentially neutral particle" it is meant that the particle has surface zeta potential of between −15 mV and +15 mV. In general neutrality of the particle is controlled by selection of a neutral emulsifier as the amphiphile during manufacture of the particles. For example, particles such as, but not limited to, solid lipid particles, polymer particles, polymerosomes, and micellar particles will be neutral if a neutral emulsifier such as, but not limited to, TWEEN® 20, Brij700, Brij58, poloxamer, or PEO are used as the amphiphile. Additional exemplary amphiphiles useful in the present invention include, but are not limited to, finely divided solids having a contact angle against the solution in which the particles are dispersed in, that is around 90 degrees so that it sits at the interface between the particle and the liquid (see, for example, ucm with the extension es/info/mclab/publications/Langmuir21_2005_Melle.pdf of the world wide web), emulsifiers such as polyethylene glycol, poly(vinyl alcohol) poly(vinylpyrrolidinone), Pluronic (PEO-PPO-PEO) block copolymers), poly(oxyethylene) sorbitan fatty acid esters (Tweens), polyoxyethylene alkyl ethers (Brij series), sorbitan fatty acid esters (Span series), polyethyleneoxide fatty acid esters, and the like.

In a preferred embodiment of the aerosols of the present invention, the essentially neutral colloidal particles further comprise one or more active pharmaceutical ingredients. In this embodiment, one or more active pharmaceutical ingredients may be incorporated within or encapsulated by the essentially neutral colloidal particle. Alternatively, or in addition, one or more active pharmaceutical ingredients may be attached to a surface of the essentially neutral particle. Means by which the active pharmaceutical agent attaches to the particle is dependent upon the characteristics of the pharmaceutically active ingredient and the particles. For example, proteins readily adsorb or attach to hydrophobic particles via hydrophobic interactions with the particle surface, and displace some of the neutral emulsifier. The active pharmaceutical ingredient can also be attached to neutral particles when the amphiphile that keeps the particle stable has a reactive chemical group on it that allows for formation of a chemical bond between the active pharmaceutical ingredient and the amphiphile. For example, an amphiphile such as an emulsifier containing a terminal aldehyde group can be used to attach an active pharmaceutical ingredient such as protein via the amine group on the protein.

Active pharmaceutical agents or ingredients which can be encapsulated or attached to a particle and aerosolized in accordance with the present invention include, but are in no way limited to, drugs, including vaccines, nutritional agents, cosmeceuticals and diagnostic agents. Examples of active pharmaceutical agents or ingredients for use in the present invention include, but are not limited to analgesics, anti-anginal agents, anti-asthmatics, anti-arrhythmic agents, anti-angiogenic agents, antibacterial agents, anti-benign prostate hypertrophy agents, anti-cystic fibrosis agents, anti-coagulants, anti-depressants, anti-diabetic agents, anti-epileptic agents, anti-fungal agents, anti-gout agents, anti-hypertensive agents, anti-inflammatory agents, anti-malarial agents, anti-migraine agents, anti-muscarinic agents, anti-neoplastic agents, anti-obesity agents, anti-osteoporosis agents, anti-parkinsonian agents, anti-protozoal agents, anti-thyroid agents, anti-urinary incontinence agents, anti-viral agents, anxiolytics, beta-blockers, cardiac inotropic agents, cognition enhancers, corticosteroids, COX-2 inhibitors, diuretics, erectile dysfunction improvement agents, essential fatty acids, gastrointestinal agents, histamine receptor antagonists, hormones, immunosuppressants, keratolyptics, leukotriene antagonists, lipid regulating agents, macrolides, muscle relaxants, non-essential fatty acids, nutritional agents, nutritional oils, protease inhibitors and stimulants. Preferred for use in the formulations of the present invention are active pharmaceutical agents or ingredients used to treat lung disorders such as, but not limited to, anti-asthmatics, anti-cystic fibrosis agents, anti-emphysema agents and anti-neoplastic drugs.

In some embodiments, the particle itself can act as a therapeutic agent thereby causing a desired biological response. In this embodiment the formulation comprises particles without an additional active pharmaceutical ingredient.

Another aspect of the present invention relates to methods for producing a formulation comprising a plurality of aqueous droplets, each droplet of the plurality comprising an essentially neutral colloidal particle stabilized by an amphiphile and sized to fit inside the droplet. In such methods, on average each aqueous droplet contains at least one essentially neutral particle sized to fit within the droplet. The aerosol may further comprise aqueous droplets which contain no particles.

Methods of the present invention vary depending upon the particles and/or active pharmaceutical ingredient or agent used.

In one embodiment, wherein solid lipid or wax particles are used, the method comprises heating the solid lipid or wax above its melt temperature to form a molten lipid or wax. The active pharmaceutical ingredient, preferably an oil soluble active pharmaceutical ingredient is then added along with an amphiphile such as a non-ionic emulsifier and the particles are formed using high shear such as that provided by an ultrasonic horn, or a high-pressure homogenizer, until the particle size of the dispersed phase is submicron. The thus-formed hot oil-in-water nanoemulsion is then cooled to room temperature to harden the lipid or wax nanodroplets, forming an aqueous dispersion of neutrally charged, active pharmaceutical ingredient-containing lipid or wax nanoparticles, stabilized by the non-ionic emulsifier. This formulation is suitable to be nebulized into an aerosol for inhalation, delivering the active pharmaceutical ingredient to the lungs. An advantage of this process is that no hazardous organic solvents are required in the production of the neutral active pharmaceutical-containing nanoparticles.

In an alternative embodiment, the formulation of the present invention is prepared from an oil-in-water emulsion. In this embodiment, the active pharmaceutical ingredient is dispersed or dissolved in an oil phase comprising a pharmaceutically acceptable oil, or mixture of oils, such as but not limited to mineral oil, silicone oil, olive oil, squalene and/or squalane, which is then emulsified into an aqueous non-ionic emulsifier with high shear until the particles are submicron.

In another embodiment, wherein the particles are polymersomes, the method comprises mixing a hydrophobic active pharmaceutical ingredient with an amphiphilic block copolymer known to form polymersomes so that a film is formed. The film is hydrated with water, and extruded through a porous membrane to form polymersomes containing active pharmaceutical ingredient in the hydrophobic portion of the bilayer. Alternatively, water soluble active pharmaceutical ingredients can be added to the water used for hydration of the film so that the active pharmaceutical ingredient is encapsulated in the aqueous core of the polymersome.

In another embodiment wherein the particles are micelles, the method comprises adding a hydrophobic active pharmaceutical ingredient to a solution of non-ionic emulsifier above the critical micelle concentration of the emulsifier. In this embodiment, the active pharmaceutical ingredient is dissolved in the core of the micelles.

Another aspect of the present invention relates to the use of these formulations and aerosol in treating a subject in need thereof. Aerosols of the present invention can be administered to a subject via a device that can produce an aerosol with an average droplet size between around 1-50 microns, more preferably 1-10 microns. Examples of such devices include but are not limited to nebulizers, metered dose inhalers and nasal spray devices.

An aqueous dispersion of natural wax particles having an average particles size of about 400 nm was prepared.

This nanoparticle dispersion was prepared from carnauba wax at 10% solids, stabilized with a non-ionic emulsifier (either Brij700 or TWEEN®20), without the use of hazardous organic solvents. The aqueous dispersion was then aerosolized in accordance with the present invention by an OTC nebulizer.

For this experiment, the mouthpiece of the nebulizer was placed in the sample opening of a Laser diffraction particle sizer (Sympatec). The nebulizer was filled with a 10% dispersion of wax nanoparticles stabilized by TWEEN®20, then switched on to generate a nebulized mist which was drawn into the Sympatec laser path by air flow. The light scattered from the aerosol was detected and converted to particles size distribution by Sympatec software. Data were collected over 10 seconds per run. FIG. 1 provides data from several runs overlaid for reproducibility.

In addition, a 10% wax nanoparticle dispersion made of yellow carnauba wax stabilized by TWEEN®20 emulsifier was nebulized using the MisterNeb™ nebulizer (Respironics, Cedar Grove, N.J.). The resulting aerosol was passed through a next-generation cascade impactor (NGI, MSP Corp., Minneapolis, Minn.)) at a flow rate of about 15 L/minute. The aerosol droplets are separated in the NGI according to their aerodynamic size as the air stream containing the droplets passes through the variously sized holes in each stage of the NGI. Results from this experiment are shown in FIG. 2.

Figure 2:
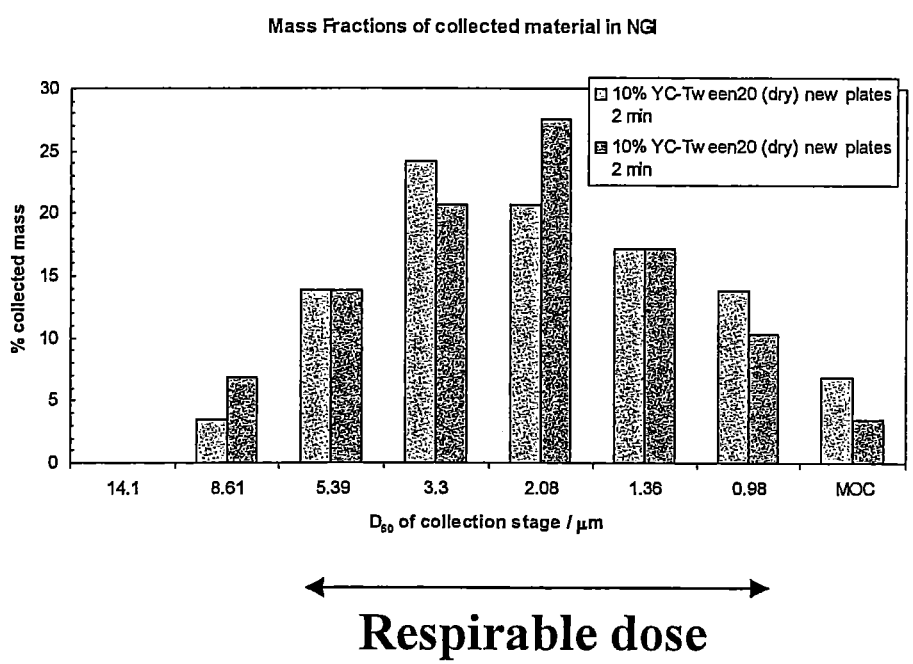
FIG. 2 is a bar graph showing the particles from the aerosol of the present invention to be deposited ideally for pulmonary delivery.

As shown in FIG. 1 and FIG. 2, the majority of aqueous droplets of the aerosol were in the range of about 1-5 microns, a preferred size for lung delivery. Further, the aqueous droplets contained the carnauba wax nanoparticles as a stable dispersion exhibiting the same properties as the initial bulk dispersion.

The ability to encapsulate an active pharmaceutical ingredient in accordance with the formulations and methods of the present invention was confirmed using the fluorescent dye pyrromethene 567A.

A formulation of the present invention comprising particles encapsulating an antiretroviral compound was also prepared.

In addition, water-soluble pharmaceutical ingredients, in particular, proteins and oligonucleotides were attached to the surface of these particles simply by mixing the two. Proteins are attached to the surface of neutral particles preferably by mixing the protein with a neutral emulsifier during the preparation of the particles.

Thus, as demonstrated by these experiments, aqueous dispersions of essentially neutral colloidal particles are useful for encapsulating active pharmaceutical ingredients, preferably hydrophobic active pharmaceutical ingredients, or surface attaching hydrophilic active pharmaceutical ingredients, or combinations thereof, to produce stable formulations useful for delivery as aerosols to the lung.

The following nonlimiting examples are provided to further illustrate the present invention.

EXAMPLES

Example 1

Preparation of Aqueous Dispersion of Natural Wax Particles

Nanoparticle dispersions of carnauba wax at 10% solids, stabilized with a non-ionic emulsifier (either Brij700 or TWEEN® 20), were prepared without the use of hazardous organic solvents. The particle size was determined by photon correlation spectroscopy (Brookhaven Instruments, N.Y.).

Example 2

Aerosolization of Aqueous Dispersion of Natural Wax Particles by Nebulizer

The 10% solids aqueous dispersion of Example 1 was aerosolized by a MisterNeb™ OTC nebulizer. 10 mL of the dispersion was placed in the nebulizer chamber, and the nebulizer turned on. The droplets of an aerosol thus generated were sized using a Sympatec (NJ) laser diffraction particle-sizer and the results showed particles with a $D_{50}$ diameter of 4.8 microns, and $D_{90}$ diameter of 9.5 microns. The dispersion was nebulized into a next-generation cascade impactor and the majority of wax nanoparticles were recovered from the stage where 2 micron droplets are expected to collect, showing that the wax particles should be readily delivered to the lung and that the 5 micron starting droplets probably partially evaporated during flight through the cascade impactor.

A dispersion of nanoparticles containing a fluorescent dye was also nebulized and the aerosol was fluorescent under "black light" illumination, indicating the dye was present in the aerosol. Separately the particles were removed from a portion of the dispersion by filtration, and the fluorescence of the supernatant was determined as zero thus showing that the fluorescence of the aerosol was purely from the fluorescence of the nanoparticles containing the dye which themselves were located in the aerosolized droplets.

Separately, a dispersion was nebulized, and the aerosol droplets collected and condensed to re-form a bulk dispersion. The mean particle size of the initial dispersion was 480 nm and the mean particle size of the re-formed dispersion from condensing the collected aerosol was 482 nm indicating that the nanoparticles are stable in the aerosol droplets.

Example 3

Preparation of Aqueous Dispersion of Natural Wax Particles Encapsulating an API

An aqueous dispersion of a water insoluble antiretroviral compound encapsulated within the wax particles was prepared. For this dispersion, a wax phase was first prepared by adding 0.1% of the antiretroviral to a molten mixture of carnauba wax containing 10% octylmethoxycinnamate. To this sufficient hot water containing 1% Brij700 was added with ultrasonication, to form a 10% w/w dispersion of the wax phase in water. The supernatant was assayed for the antiretroviral with a negative result, indicating all the drug was encapsulated within the wax particles.

What is claimed is:

1. A method for producing an aerosol without requiring a hazardous organic solvent, said method comprising:
   heating a solid lipid or wax above its melt temperature to form a molten lipid or wax;
   adding an active pharmaceutical ingredient and amphiphile to the molten lipid or wax to form an emulsion;
   forming submicron particles using high shear in the emulsion; and
   cooling the emulsion and particles to room temperature to form the aerosol, wherein the aerosol comprises a plurality of aqueous droplets, each aqueous droplet of said plurality comprising:
   an essentially neutral colloidal particle sized to fit inside the droplet, wherein the essentially neutral particle is selected from the group consisting of a polymer, a solid lipid, a natural or synthetic wax, a pharmaceutically acceptable oil, a micelle, a polymersome, a vesicle, a polyplex, a coacervate and an inorganic particle; and
   an active pharmaceutical agent incorporated within the essentially neutral particle or attached to a surface of the essentially neutral particle.

2. The method of claim 1 wherein the aerosol of aqueous droplets is produced by a nebulizer.

3. The method of claim 1 wherein the aerosol of aqueous droplets is produced by a metered dose inhaler.

4. The method of claim 1 wherein the aerosol of aqueous droplets is produced by an aerosol generating device.

5. The method of claim 1 wherein the aqueous droplets have a mean droplet size of 50 microns in diameter or less.

6. The method of claim 5 wherein the mean droplet size is less than 10 microns.

7. The method of claim 5 wherein the mean droplet size is 1 to 5 microns.

8. The method of claim 1 wherein the essentially neutral particle is stabilized by an amphiphile.

9. The method of claim 8 wherein the amphiphile is a surfactant, a polymeric stabilizer or a finely divided solid having a contact angle against a solution in which the particles are dispersed in, that is around 90 degrees so that it sits at the interface between the particle and the liquid.

10. The method of claim 1 wherein the active pharmaceutical agent is incorporated within the essentially neutral particle.

11. The method of claim 1 wherein the active pharmaceutical agent is attached to a surface of the essentially neutral particle.

12. A method for delivering an active pharmaceutical agent to the pulmonary system of a subject in need of the active pharmaceutical agent comprising administering to the subject via inhalation an aerosol produced by the method of claim 1.

13. The method of claim 12 wherein the aerosol is administered via a device that can produce an aerosol with an average droplet size between 1-10 microns.

14. The method of claim 13 wherein the device is a nebulizer.

15. The method of claim 13 wherein the device is a metered dose inhaler.

* * * * *